US007056502B2

(12) United States Patent
Hildinger et al.

(10) Patent No.: US 7,056,502 B2
(45) Date of Patent: Jun. 6, 2006

(54) RECOMBINANT AAV VECTORS WITH AAV5 CAPSIDS AND AAV5 VECTORS PSEUDOTYPED IN HETEROLOGOUS CAPSIDS

(75) Inventors: Markus Hildinger, Boston, MA (US); James M. Wilson, Gladwyne, PA (US); Alberto Auricchio, Napoli (IT)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 331 days.

(21) Appl. No.: 10/257,961

(22) PCT Filed: Apr. 23, 2001

(86) PCT No.: PCT/US01/13000

§ 371 (c)(1),
(2), (4) Date: Oct. 25, 2002

(87) PCT Pub. No.: WO01/83692

PCT Pub. Date: Nov. 8, 2001

(65) Prior Publication Data

US 2004/0052764 A1 Mar. 18, 2004

Related U.S. Application Data

(60) Provisional application No. 60/200,409, filed on Apr. 28, 2000.

(51) Int. Cl.
*A61K 48/00* (2006.01)
*C12N 15/864* (2006.01)

(52) U.S. Cl. .................... 424/93.2; 424/93.1; 424/93.6; 435/320.1; 435/325; 435/455; 435/456; 435/457

(58) Field of Classification Search ............. 435/320.1, 435/325, 366, 455, 456, 457; 424/93.1, 93.2, 424/93.6
See application file for complete search history.

(56) References Cited

U.S. PATENT DOCUMENTS

| 5,866,552 | A | 2/1999 | Wilson et al. |
| 6,203,975 | B1 | 3/2001 | Wilson et al. |
| 6,759,237 | B1 | 7/2004 | Wilson et al. |
| 6,855,314 | B1 | 2/2005 | Chiorini et al. |
| 2003/0053990 | A1* | 3/2003 | Rabinowitz et al. ....... 424/93.2 |
| 2004/0057931 | A1 | 3/2004 | Wilson et al. |
| 2004/0057932 | A1 | 3/2004 | Wilson et al. |
| 2004/0057933 | A1 | 3/2004 | Wilson et al. |
| 2004/0086490 | A1* | 5/2004 | Chiorini et al. ............ 424/93.2 |

FOREIGN PATENT DOCUMENTS

| WO | WO 96/00587 | 1/1996 |
| WO | WO 98/09657 | 3/1998 |
| WO | WO 99/61601 | 12/1999 |
| WO | WO 01/70276 | 9/2001 |

OTHER PUBLICATIONS

Xiao X., Production of High-Titer Recombinant Adeno-Associated Virus Vectors in the Absence of Helper Adenovirus, Journal of Virology, p. 2224-2232, vol. 72, No. 3, (Mar. 1998), XP002924402.
C. Balague, Adeno-Associated Virus Rep 78 Protein and Terminal Repeats Enhance Integration of DNA Sequences into the Cellular Genome, Journal of Virology, vol. 71, No. 4, p. 3299-3306 (Apr. 1997).
K. Berns, Parvovirus Replication, Microbiological Reviews, vol. 54, No. 3, p. 316-329, (Sep. 1990).
K. Berns, Parvoviridae: The Viruses and Their Replication, Fundamental Virology, Third Edition, p. 1017-1041, (Lippincott-Raven Publishers, Philadelphia, PA) (1996) (No month available).
J. Chiorini, Cloning and Characterization of Adeno-Associated Virus Type 5, Journal of Virology, vol. 73, No. 2, p. 1309-1319, (Feb. 1999).
K. Fisher, Recombinant Adeno-Associated Virus for Muscle Directed Gene Therapy, Nature Medicine, vol. 3, No. 3, (Mar. 1997).
R. Kotin, Site-Specific Integration by Adeno-Associated Virus, Proc. Natl. Acad. Sci. USA, vol. 87, p. 2211-2215, (Mar. 1990).
N. Muzyczka, Use of Adeno-Associated Virus as a General Transduction Vector for Mammalian Cells, Current Topics in Microbiology and Immunology, vol. 158, p. 97-129, (1992) (No month available).
Samulski, Targeted Integration of Adeno-Associated Virus (AAV) into Human Chromosome 19, EMBO Journal, vol. 10, No. 12, pp. 3941-3950 (Dec. 1991).
Snyder, Features of the Adeno-Associated Virus Origin Involved in Substrate Recognition by the Viral Rep Protein, Journal of Virology, vol. 67, No. 10, pp. 6096-6104, (Oct. 1993).
Snyder, Persistent and Therapeutic Concentrations of Human Factor IX in Mice After Hepatic Gene Transfer of Recombinant AAV Vectors, Nature Genetics, vol. 16, pp. 270-276 (Jul. 1997).
R. Surosky, Adeno-Associated Virus Rep Proteins Target DNA Sequences to a Unique Locus in the Human Genome, Journal of Virology, vol. 71, pp. 7951-7959 (Oct. 1997).
Xiao, Gene Transfer by Adeno-Associated Virus Vectors into the Central Nervous System, Experimental Neurology, 144, pp. 113-124 (Mar. 1997).

(Continued)

*Primary Examiner*—David Guzo
(74) *Attorney, Agent, or Firm*—Howson and Howson

(57) ABSTRACT

A pseudotyped rAAV is described, which contains sequences derived from AAV5. A method for producing rAAV pseudotyped with AAV5 capsid is described in which the rep proteins of the serotype or any cross-reactive serotype of the AAV ITRs are utilized. A similar method may be provided to generate a pseudotyped rAAV in which minigenes carrying AAV5 ITRs are packaged in capsids of a heterologous AAV serotype. Also provided are pharmaceutical compositions containing the pseudotyped rAAV and methods of using them for gene delivery.

6 Claims, 2 Drawing Sheets

OTHER PUBLICATIONS

Xiao, Efficient Long-Term Gene Transfer into Muscle Tissue of Immunocompetent Mice by Adeno-Associated Virus Vector, Journal of Virology, vol. 70, pp. 8098-8108, (Nov. 1996).

Wilson, Method for Recombinant Adeno-Associated Virus-directed Gene Therapy, Publication No. U.S.-2001-0006955-A1, (publication date: Jul. 5, 2001).

Wilson, Method for Recombinant Adeno-Associated Virus-Directed Gene Therapy, Publication No. U.S.-2002-0037867-A1 (publication date: Mar. 28, 2002).

Surace et al, Delivery of Adeno-Associated Virus Vectors to the Fetal Retina: Impact of Viral Capsid Proteins on Retinal Neuronal Progenitor Transduction, Journal of Virology, vol. 77, No. 14, pp. 7957-7963, (Jul. 2003).

* cited by examiner

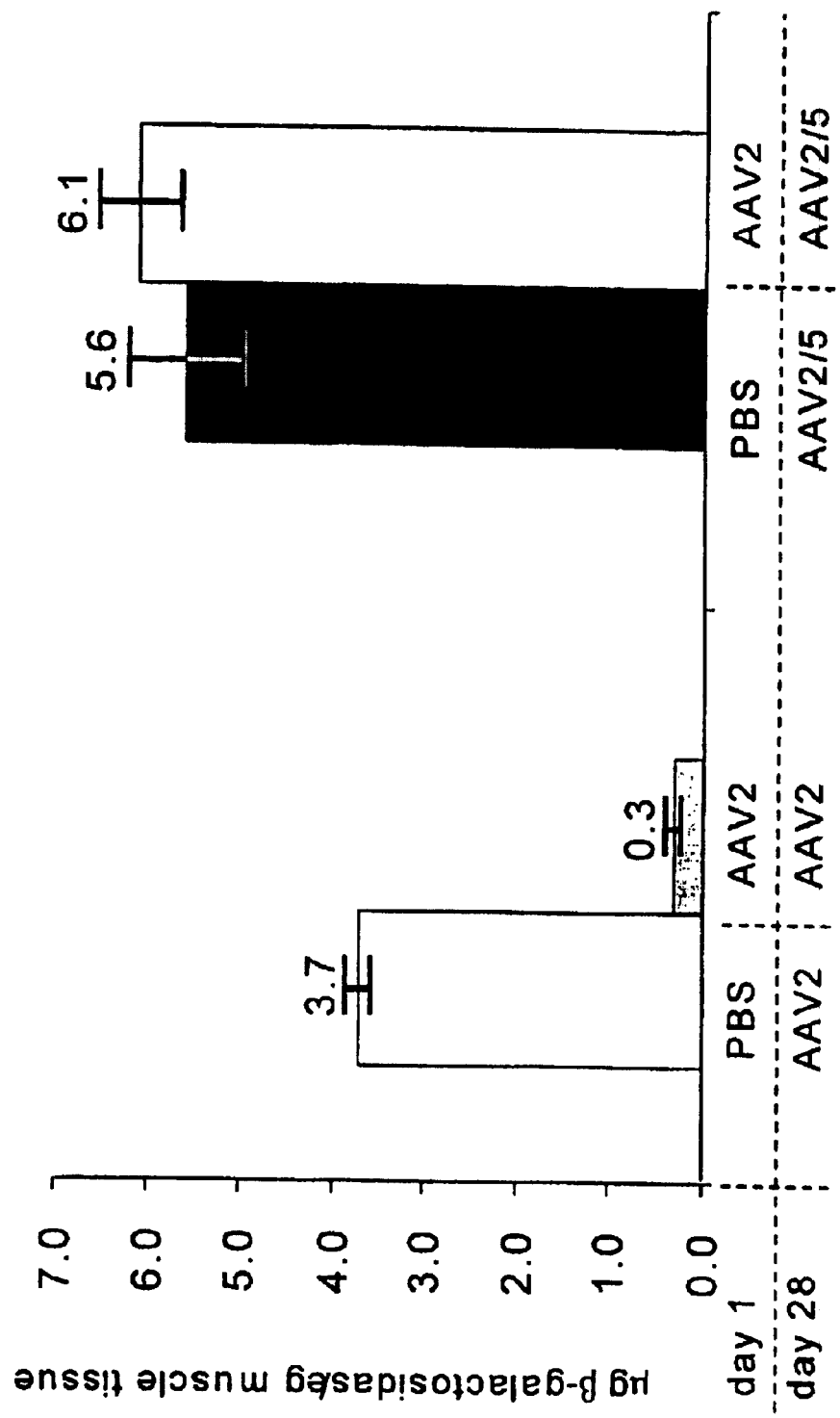

SEQUENCE LISTING

```
<160> NUMBER OF SEQ ID NOS: 18

<210> SEQ ID NO 1
<211> LENGTH: 26
<212> TYPE: DNA
<213> ORGANISM: Artificial Sequence
<220> FEATURE:
<223> OTHER INFORMATION: synthetic primer

<400> SEQUENCE: 1
aagctagcta gttattaata gtaatc                                        26

<210> SEQ ID NO 2
<211> LENGTH: 28
<212> TYPE: DNA
<213> ORGANISM: Artificial Sequence
<220> FEATURE:
```

<223> OTHER INFORMATION: synthetic primer

<400> SEQUENCE: 2
aactgcagga tctgacggtt cactaaac                                28

<210> SEQ ID NO 3
<211> LENGTH: 26
<212> TYPE: DNA
<213> ORGANISM: Artificial Sequence
<220> FEATURE:
<223> OTHER INFORMATION: synthetic primer

<400> SEQUENCE: 3
aactgcagaa gttggtcgtg aggcac                                  26

<210> SEQ ID NO 4
<211> LENGTH: 30
<212> TYPE: DNA
<213> ORGANISM: Artificial Sequence
<220> FEATURE:
<223> OTHER INFORMATION: synthetic primer

<400> SEQUENCE: 4
aagcggccgc ctggacacct gtggagaaag                              30

<210> SEQ ID NO 5
<211> LENGTH: 31
<212> TYPE: DNA
<213> ORGANISM: Artificial Sequence
<220> FEATURE:
<223> OTHER INFORMATION: synthetic primer

<400> SEQUENCE: 5
aagcggccgc catgaccatg attacggatt c                            31

<210> SEQ ID NO 6
<211> LENGTH: 26
<212> TYPE: DNA
<213> ORGANISM: Artificial Sequence
<220> FEATURE:
<223> OTHER INFORMATION: synthetic primer

<400> SEQUENCE: 6
ttggatcctt atttttgaca ccagac                                  26

<210> SEQ ID NO 7
<211> LENGTH: 26
<212> TYPE: DNA
<213> ORGANISM: Artificial Sequence
<220> FEATURE:
<223> OTHER INFORMATION: synthetic primer

<400> SEQUENCE: 7
aaggatccaa tcaacctctg gattac                                  26

<210> SEQ ID NO 8
<211> LENGTH: 28
<212> TYPE: DNA
<213> ORGANISM: Artificial Sequence
<220> FEATURE:
<223> OTHER INFORMATION: synthetic primer

<400> SEQUENCE: 8
ttagatctcg aagacgcgga agaggccg                                28

<210> SEQ ID NO 9
<211> LENGTH: 29
<212> TYPE: DNA
<213> ORGANISM: Artificial Sequence
<220> FEATURE:
<223> OTHER INFORMATION: synthetic primer

<400> SEQUENCE: 9
tttagatctg cctcgactgt gccttctag                              29

<210> SEQ ID NO 10
<211> LENGTH: 29
<212> TYPE: DNA
<213> ORGANISM: Artificial Sequence
<220> FEATURE:
<223> OTHER INFORMATION: synthetic primer

<400> SEQUENCE: 10
aactcgagtc cccagcatgc ctgctattg                              29

<210> SEQ ID NO 11
<211> LENGTH: 42
<212> TYPE: DNA
<213> ORGANISM: Artificial Sequence
<220> FEATURE:
<223> OTHER INFORMATION: synthetic primer

<400> SEQUENCE: 11
agttactctt cttgcttgtt aatcaataaa ccgtttaatt cg               42

<210> SEQ ID NO 12
<211> LENGTH: 44
<212> TYPE: DNA
<213> ORGANISM: Artificial Sequence
<220> FEATURE:
<223> OTHER INFORMATION: synthetic primer

<400> SEQUENCE: 12
agttactctt cacctgattt aaatcattta ttgttcaaag atgc             44

<210> SEQ ID NO 13
<211> LENGTH: 46
<212> TYPE: DNA
<213> ORGANISM: Artificial Sequence
<220> FEATURE:
<223> OTHER INFORMATION: synthetic primer

<400> SEQUENCE: 13
agttactctt ccaggtatgt cttttgttga tcaccctcca gattgg           46

<210> SEQ ID NO 14
<211> LENGTH: 45
<212> TYPE: DNA
<213> ORGANISM: Artificial Sequence
<220> FEATURE:
<223> OTHER INFORMATION: synthetic primer

<400> SEQUENCE: 14
agttactctt cagcaattaa agggtcggg taaggtatcg ggttc             45

<210> SEQ ID NO 15
<211> LENGTH: 47
<212> TYPE: DNA
<213> ORGANISM: Artificial Sequence
<220> FEATURE:
<223> OTHER INFORMATION: synthetic primer

```
<400> SEQUENCE: 15
aaactcgaga ttgctagctc actgcttaca aaaccccctt gcttgag                        47

<210> SEQ ID NO 16
<211> LENGTH: 26
<212> TYPE: DNA
<213> ORGANISM: Artificial Sequence
<220> FEATURE:
<223> OTHER INFORMATION: synthetic primer

<400> SEQUENCE: 16
ttcacagctt acaacatcta caaaac                                              26

<210> SEQ ID NO 17
<211> LENGTH: 33
<212> TYPE: DNA
<213> ORGANISM: Artificial Sequence
<220> FEATURE:
<223> OTHER INFORMATION: synthetic primer

<400> SEQUENCE: 17
aaagcggccg ccatggtgag caagggcgag gag                                      33

<210> SEQ ID NO 18
<211> LENGTH: 39
<212> TYPE: DNA
<213> ORGANISM: Artificial Sequence
<220> FEATURE:
<223> OTHER INFORMATION: synthetic primer

<400> SEQUENCE: 18
aaggatccaa gcttattact tgtacagctc gtccatgcc                                39
```

RECOMBINANT AAV VECTORS WITH AAV5 CAPSIDS AND AAV5 VECTORS PSEUDOTYPED IN HETEROLOGOUS CAPSIDS

CROSS-REFERENCE TO RELATED APPLICATIONS

This is a national stage of PCT/US01/13000, filed Apr. 23, 2001, which claims the benefit of the priority of U.S. Patent Application No. 60/200,409, filed Apr. 28, 2000.

This work was funded, in part, by a grant from the National Institutes of Health (NIH) P30 DK47757-07 and P01 HL59407-02. The US government has certain rights in this invention.

BACKGROUND OF THE INVENTION

The invention relates generally to the field of viral vectors useful in gene delivery, and more particularly, to recombinant adeno-associated viruses (rAAV).

Adeno-associated viruses are small, single-stranded DNA viruses which require helper virus to facilitate efficient replication (K. I. Berns, Parvoviridae: the viruses and their replication, p. 1007–1041, in F. N. Fields et al., FUNDAMENTAL VIROLOGY, 3rd ed., vol. 2, (Lippencott-Raven Publishers, Philadelphia, Pa.) (1995)). The 4.7 kb genome of AAV is characterized by two inverted terminal repeats (ITR) and two open reading frames which encode the Rep proteins and Cap proteins, respectively. The Rep reading frame encodes four proteins of molecular weight 78 kD, 68 kD, 52 kD and 40 kD. These proteins function mainly in regulating AAV replication and integration of the AAV into a host cell's chromosomes. The Cap reading frame encodes three structural proteins of molecular weight 85 kD (VP 1), 72 kD (VP2) and 61 kD (VP3) (Berns, cited above). More than 80% of total proteins in AAV virion comprise VP3. The two ITRs are the only cis elements essential for AAV replication, packaging and integration. There are two conformations of AAV ITRs called "flip" and "flop". These differences in conformation originated from the replication model of adeno-associated virus which uses the ITR to initiate and re-initiate the replication (R. O. Snyder et al., J. VIROL., 67:6096–6104 (1993); K. I. Berns, MICROBIOLOGICAL REVIEWS, 54:316–329 (1990)).

AAVs have been found in many animal species, including primates, canine, fowl and human (F. A. Murphy et al., "The Classification and Nomenclature of Viruses: Sixth Report of the International Committee on Taxonomy of Viruses", ARCHIVES OF VIROLOGY, (Springer-Verlag, Vienna) (1995)). Six primate serotypes have been reported (AAV1, AAV2, AAV3, AAV4, AAV5 and AAV6). With the exception of AAV5, which was isolated from a patient's lesion, all other AAV serotypes were discovered in cell culture. In addition, AAV5 is the only serotype which does not show cross-complementation with any other serotype. Whereas the homology among the other serotypes is in the range of 75% to 82%, AAV5 reveals only about 50% homology with other AAV serotypes on the protein level. The sequence of the AAV5 has been cloned and sequenced, and recombinant AAV5 particles have been generated (J. A. Chiorini et al, J. VIROL., 73(2):1309–1319 (February 1999)). The authors of this paper also reported that an attempt to pseudotype an AAV2 vector in an AAV5 capsid and an attempt to pseudotype an AAV5 vector in an AAV2 capsid were unsuccessful.

A number of unique properties make AAV a promising vector for human gene therapy (Muzyczka, CURRENT TOPIC IN MICROBIOLOGY AND IMMUNOLOGY, 158:97–129 (1992)). Unlike other viral vectors, AAVs have not been shown to be associated with any known human disease and are generally not considered pathogenic. Wild type AAV is capable of integrating into host chromosomes in a site specific manner (R. M. Kotin et al., PROC. NATL. ACAD. SCI, USA, 87:2211–2215 (1990); R. J. Samulski, EMBO J., 10(12): 3941–3950 (1991)). Recombinant AAV vectors can integrate into tissue cultured cells in chromosome 19 if the rep proteins are supplied in trans (C. Balague et al., J. VIROL., 71:3299–3306 (1997); R. T. Surosky et al., J. VIROL., 71:7951–7959 (1997)). The integrated genomes of AAV have been shown to allow long term gene expression in a number of tissues, including muscle, liver, and brain (K. J. Fisher, NATURE MED., 3(3):306–312 (1997); R. O. Snyder et al., NATURE GENETICS, 16:270–276 (1997); X. Xiao et al., EXPERIMENTAL NEUROLOGY, 144:113–124 (1997); Xiao, J. VIROL., 70(11):8098–8108 (1996)).

AAV2 has been shown to be present in about 80–90% of the human population. Earlier studies showed that neutralizing antibodies for AAV2 are prevalent (W. P. Parks et al., J. VIROL., 2:716–722 (1970)). The presence of such antibodies may significantly decrease the usefulness of AAV vectors based on AAV2 despite its other merits.

What are needed in the art are vectors characterized by the advantages of AAV-2, such as those described above, without the disadvantages, e.g., the presence of destructive neutralizing antibodies.

SUMMARY OF THE INVENTION

Advantageously, the present invention provides a method of pseudotyping AAV viruses by packaging AAV minigenes in AAV capsids utilizing ITRs and/or capsids derived from AAV5. The inventors have found that the use of the rep protein from the same ITRs as are in the AAV minigene (or a cross-reactive serotype) allows packaging of the vector in a capsid protein from a heterologous serotype. The ability to pseudotype rAAV in an AAV5 capsid, which is not recognized by antibodies to other AAV serotype capsid proteins, provides significant advantages for repeat delivery of a rAAV carrying a selected transgene.

In one aspect, the present invention provides a rAAV in which an AAV5 capsid contains an rAAV minigene comprising AAV 5' ITRs, a heterologous molecule for delivery to a host cell, and AAV 3' ITRs, wherein the ITRs of a serotype heterologous to AAV5.

In another aspect, the invention provides a rAAV in which an AAV5 minigene is packaged in a capsid of a serotype heterologous to AAV5.

In yet another aspect, the invention provides a host cell containing a rAAV of the invention.

In a further aspect, the invention provides a method of packaging an AAV minigene in an AAV5 capsid. This method involves culturing in a host cell an AAV minigene to be packaged, an AAV5 capsid protein, and a functional portion of an AAV rep of the same or a cross-reactive serotype as the minigene, wherein said AAV rep is a non-serotype 5 AAV. The host cell is cultured in the presence of sufficient helper functions to permit packaging of the minigene in the AAV5 capsid.

In yet a further aspect, the invention provides a method of packaging a minigene containing AAV5 ITRs in a non-AAV5 capsid. This method involves culturing in a host cell an AAV5 minigene to be packaged, a non-AAV5 capsid protein, and a functional portion of an AAV5 rep in the presence of sufficient helper functions to permit replication and packaging of the minigene in the non-AAV5 capsid.

In still another aspect, the invention provides a packaging host cell containing an AAV minigene to be packaged, an AAV capsid protein; a functional portion of an AAV rep of the same or a cross-reactive serotype as the ITRs in the AAV minigene, in the presence of sufficient helper functions to permit packaging of the minigene in the AAV5 capsid.

In a further aspect, the invention provides a rAAV5, which contains modified 5' AAV5 terminal repeat sequences, a heterologous molecule for delivery to the host cell, and modified 3' AAV5 terminal repeat sequences.

In still a further aspect, the present invention provides a pharmaceutical composition comprising a carrier and a rAAV of the invention.

In yet another aspect, the present invention provides a method for AAV-mediated delivery of a heterologous molecule to a host involving the step of delivering to a selected host a recombinant AAV comprising an AAV minigene which contains a heterologous molecule for delivery to a host cell and in an AAV5 capsid in which the minigene is packaged. In one embodiment, the AAV vector comprises ITRs of a serotype heterologous to AAV5.

In still another aspect, the present invention provides a method for AAV-mediated delivery of a heterologous molecule to a host involving the step of delivering to a selected host a recombinant AAV vector comprising an AAV5 minigene comprising the heterologous molecule and AAV capsid in which the AAV5 minigene is packaged. In one embodiment, the AAV capsid is of a serotype heterologous to AAV5.

In another aspect, the invention provides a method for in vitro production of a selected gene product using a vector of the invention.

Other aspects and advantages of the invention will be readily apparent to one of skill in the art from the detailed description of the invention.

BRIEF DESCRIPTION OF THE DRAWINGS

FIG. 1A is a bar chart providing the results of a study to determine the effect of neutralizing antibodies to AAV 2 on vector readministration as described in Example 5A.

DETAILED DESCRIPTION OF THE INVENTION

Figure 1B:
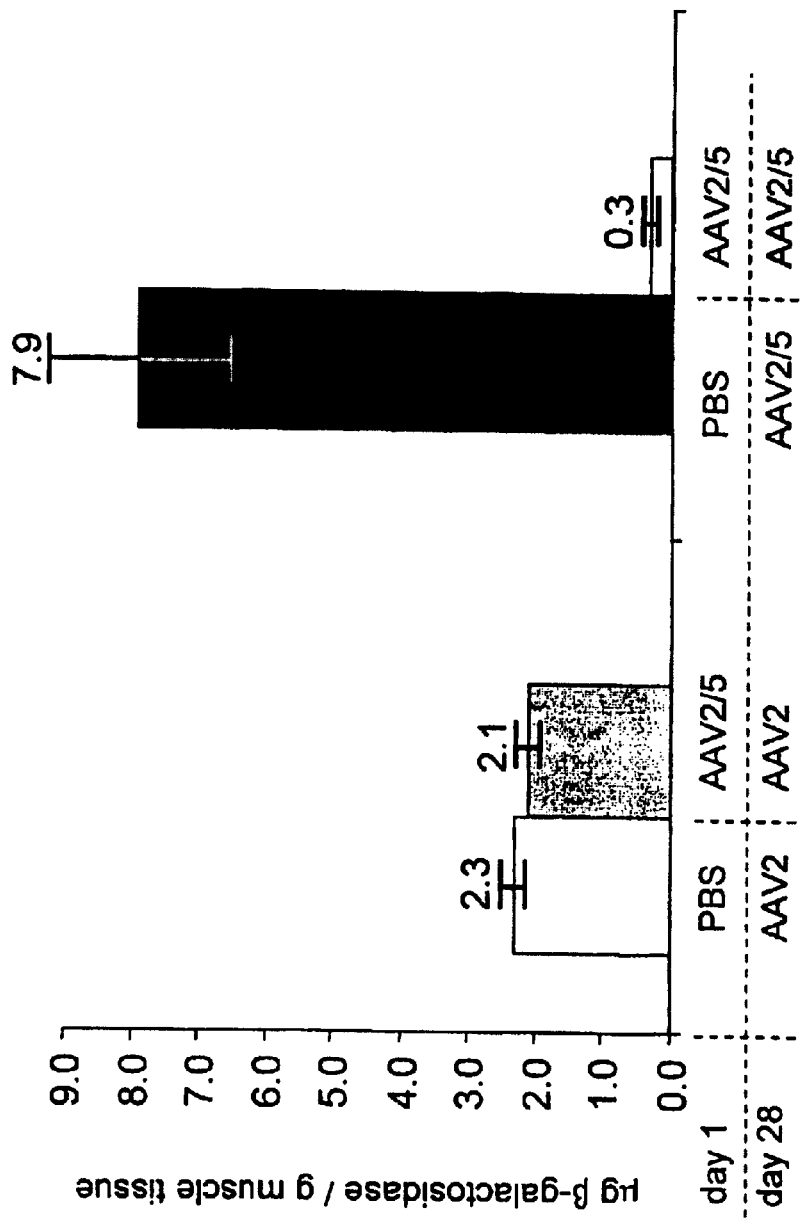
FIG. 1B is a bar chart providing the results of a study to determine the effect of neutralizing antibodies to AAV 2 on vector readministration, as described in Example 5B.

As described herein, the rAAV of the invention which are composed of the AAV5 capsid proteins and/or AAV5 ITRs are particularly well suited for use in applications in which the neutralizing antibodies diminish the effectiveness of other AAV serotype based vectors, as well as other viral vectors. The rAAV vectors of the invention are particularly advantageous in applications where readministration of rAAV is desired or required. Additionally, AAV5 has been found to have tissue tropism for muscle, intestine and lung. Thus, the rAAV of the invention having AAV5 capsids are particularly well suited for delivery of a desired product to muscle intestine and lung cells.

These and other embodiments and advantages of the invention are described in more detail below.

I. Recombinant Adeno-Associated Virus

The present invention provides recombinant adeno-associated virus (rAAV) in which AAV minigenes are packaged in an AAV capsid. In one embodiment, the present invention provides AAV minigenes pseudotyped in a capsid of a heterologous AAV serotype, in which either the AAV ITR sequences of the minigene and/or the capsid are of AAV serotype 5 (AAV5). In another embodiment, the invention provides a rAAV virus, in which both the AAV ITRs and capsid proteins are of serotype 5. In this embodiment, the rAAV contains modified 5' and/or 3' ITRs, as described herein.

As used herein, a "minigene" refers to a construct composed of, at a minimum, AAV ITRs and a heterologous molecule. These components are defined in more detail below. For production of rAAV according to the invention, a minigene may be carried on any suitable vector, including viral vectors, plasmid vectors, and the like.

A "pseudotyped" AAV of the invention refers to a recombinant AAV in which the capsid protein is of a serotype heterologous to the serotype(s) of the ITRs of the minigene. For example, a pseudotyped rAAV may be composed of a minigene carrying AAV5 ITRs and capsid of AAV2, AAV1, AAV3, AAV4, AAV6, or another suitable AAV serotype, where the minigene is packaged in the heterologous capsid. Alternatively, a pseudotyped rAAV may be composed of an AAV5 capsid which has packaged therein a minigene containing ITRs from at least one of the other serotypes.

The AAV sequences used in generating the minigenes, vectors, and capsids, and other constructs used in the present invention may be obtained from a variety of sources. For example, the sequences may be provided by AAV type 5, AAV type 2, AAV type 1, AAV type 3, AAV type 4, AAV type 6, or other AAV serotypes or other densoviruses. A variety of these viral serotypes and strains are available from the American Type Culture Collection, Manassas, Va., or are available from a variety of academic or commercial sources. Alternatively, it may be desirable to synthesize sequences used in preparing the vectors and viruses of the invention using known techniques, which may utilize AAV sequences which are published and/or available from a variety of databases. The source of the sequences utilized in preparation of the constructs of the invention, is not a limitation of the present invention.

A. AAV Minigene

The AAV minigene contains, at a minimum, AAV inverted terminal repeat sequences (ITRs) and a heterologous molecule for delivery to a host cell. Most suitably, the minigene contains AAV 5' ITRs and 3' ITRs located 5' and 3' to the heterologous molecule, respectively. However, in certain embodiments, it may be desirable for the minigene to contain the 5' ITR and 3' ITR sequences arranged in tandem, e.g., 5' to 3' or a head-to-tail, or in another alternative configuration. In still other embodiments, it may be desirable for the minigene to contain multiple copies of the ITRs, or to have 5' ITRs (or conversely, 3' ITRs) located both 5' and 3' to the heterologous molecule. The ITRs sequences may be located immediately upstream and/or downstream of the heterologous molecule, or there may be intervening sequences. The ITRs may be selected from AAV5, or from among the other AAV serotypes, as described herein. The heterologous molecule may be any substance which is desired to be delivered to a cell, including, without limitation, a polypeptide, protein, enzyme, carbohydrate, chemical moiety, or nucleic acid sequences which may include oligonucleotides, RNA, and/or DNA.

In one embodiment, the heterologous molecule may be a nucleic acid molecule which introduces specific genetic modifications into human chromosomes, e.g., for correction of mutated genes. See, e.g., D. W. Russell & R. K. Hirata, NATURE GENETICS, 18:325–330 (April 1998). In another desirable embodiment, the heterologous molecule is a nucleic acid molecule is a transgene. As used herein, "transgene" refers to a nucleic acid sequence encoding a desired product and the regulatory sequences which direct transcription and/or translation thereof in a host cell, and permit expression of the encoded product in a host cell. Suitable encoded products and regulatory sequences are discussed in more detail below. However, the selection of the heterologous molecule delivered by the AAV minigene is not a limitation of the present invention.

1. ITR Sequences

As defined herein, an "AAV5" minigene contains ITRs of AAV serotype 5. (These sequences are illustrated, in FIG. 1 of J. A. Chiorini et al, J. VIROL, 73(2):1309–1319 (February 1999), and are available from GenBank under accession no. AF085716). Preferably, substantially the entire ITR sequences are used in the molecule, although some degree of modification of these sequences is permissible. For example, the inventors have found that it is possible to utilize a 175-bp 5' ITR (13 bp deleted at the 3' end of the 5' ITR) and an 182-bp 3' ITR (6 bp at the 5' end of the 3' ITR), whereas the art has described 188 bp 5' and 3' ITRs (Chiorini, cited above). The ability to modify these ITRs sequences is within the skill of the art.

Minigenes containing ITRs from other AAV serotypes are defined similarly. For example, an "AAV2" minigene contains AAV2 ITRs. These ITR sequences are about 145 bp in length. (See, e.g., Chiorini cited above; also, see, B. J. Carter, in "Handbook of Parvoviruses", e.g., P. Tijsser, CRC Press, pp. 155–168 (1990)). However, the present invention does not require that the minigene contain both 5' and 3' ITRs from a single serotype source. Optionally, a minigene may contain 5' ITRs from one serotype and 3' ITRs from a second serotype. For ITRs from any selected AAV serotype, as with the AAV5 ITRs, the entire ITR sequences may be used in the minigene, or minor modifications may be made to the sequences.

2. Transgene

In one embodiment, the heterologous molecule of the AAV minigene comprises a transgene. As defined above, a transgene comprises nucleic acid sequence which encodes a polypeptide, protein, enzyme or other product, of interest operatively linked to regulatory components in a manner which permits transcription, translation and/or ultimately directs expression of a product encoded by the nucleic acid sequence in a host cell.

The composition of the transgene will depend upon the use to which the rAAV of the invention will be put. For example, one type of nucleic acid sequence which may be included in a transgene includes a reporter sequence, which upon expression produces a detectable signal. Such reporter sequences include without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc.

These sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of virus is detected by assays for beta-galactosidase activity. Where the transgene is luciferase, the virus may be measured by light production in a luminometer.

However, desirably, the transgene comprises a non-marker sequence encoding a product which is useful in biology and medicine, such as proteins, peptides, anti-sense nucleic acids (e.g., RNAs), enzymes, or catalytic RNAs. The encoded product may be used to correct or ameliorate gene deficiencies, such as deficiencies in which normal genes are expressed at less than normal levels or deficiencies in which the functional gene product is not expressed. A preferred type of nucleic acid sequence carried by the transgene encodes a therapeutic protein, peptide, enzyme, or polypeptide which is expressed in a host cell. The invention further includes using multiple transgenes, e.g., to correct or ameliorate a gene defect caused by a multi-subunit protein. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. In another embodiment, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., total of the DNA encoding the subunits and the IRES is less than five kilobases. Alternatively, other methods which do not require the use of an IRES may be used for co-expression of proteins. Such other methods may involve the use of a second internal promoter, an alternative splice signal, a co- or post-translational proteolytic cleavage strategy, among others which are known to those of skill in the art.

However, the selected transgene may encode any product desirable for study. The selection of the transgene sequence is not a limitation of this invention.

Other useful products which may be encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGFα), platelet-derived growth factor (PDGF), insulin growth factors I and II (IGF-I and IGF-II), any one of the transforming growth factor β superfamily, including TGF β, activins, inhibins, or any of the bone morphogenic proteins (BMP) BMPs 1–15, any one of the heregluin/neuregulin/ARIA/neu differentiation factor (NDF) family of growth factors, nerve growth factor (NGF), brain-derived neurotrophic factor (BDNF), neurotrophins NT-3 and NT4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-17, monocyte chemoattractant protein, leukemia inhibitory factor, granulocyte-macrophage colony stimulating factor, Fas ligand, tumor necrosis factors $\alpha$ and $\beta$, interferons $\alpha$, $\beta$, and $\gamma$, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors single chain T cell receptors, class I and class II MHC molecules, as well as engineered immunoglobulins and MHC molecules. Useful gene products also include regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation, including the low density lipoprotein (LDL) receptor, high density lipoprotein (HDL) receptor, the very low density lipoprotein (VLDL) receptor, and the scavenger receptor. The transgene may also contain genes encoding products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence.

Other useful gene products include, non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a gene. Other suitable product may be readily selected by one of skill in the art. The selection of the product encoded by the transgene is not considered to be a limitation of this invention.

3. Regulatory Elements

The transgene includes appropriate sequences that are operably linked to the nucleic acid sequences encoding the product of interest to promote its expression in a host cell. "Operably linked" sequences include both expression control sequences that are contiguous with the coding sequences for the product of interest and expression control sequences that act in trans or at a distance to control the expression of the product of interest. In addition to being useful in the transgene, the regulatory elements described herein may also be used in other heterologous molecules and the other constructs described in this application.

Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein processing and/or secretion. A great number of expression control sequences, e.g., native, constitutive, inducible and/or tissue-specific, are known in the art and may be utilized to drive expression of the gene, depending upon the type of expression desired. For eukaryotic cells, expression control sequences typically include a promoter, an enhancer, such as one derived from an immunoglobulin gene, SV40, cytomegalovirus, etc., and a polyadenylation sequence which may include splice donor and acceptor sites. The polyadenylation sequence generally is inserted following the transgene sequences and before the 3' ITR sequence. In one embodiment, the bovine growth hormone polyA used. The regulatory sequences useful in the constructs of the present invention may also contain an intron, desirably located between the promoter/enhancer sequence and the gene. One possible intron sequence is also derived from SV-40, and is referred to as the SV-40 T intron sequence. Another suitable sequence includes the woodchuck hepatitis virus post-transcriptional element. (See, e.g., L. Wang and I. Verma, PROC. NATL. ACAD. SCI., (1999)). Another element that may be used in the transfer vector is an internal ribosome entry site (IRES). An IRES sequence, or other suitable systems as are discussed above, may be used to produce more than one polypeptide from a single gene transcript. An IRES (or other suitable sequence) is used to produce a protein that contains more than one polypeptide chain or to express two different proteins from or within the same cell. Selection of these and other common vector and regulatory elements are conventional and many such sequences are available. See, e.g., Sambrook et al, and references cited therein at, for example, pages 3.18–3.26 and 16.17–16.27 and Ausubel et al., CURRENT PROTOCOLS IN MOLECULAR BIOLOGY, John Wiley & Sons, New York, 1989.

In one embodiment, high-level constitutive expression desired. Examples of such promoters include, without limitation, the retroviral Rous sarcoma virus (RSV) LTR promoter (optionally with the RSV enhancer), the cytomegalovirus (CMV) promoter (optionally with the CMV enhancer) (see, e.g., Boshart et al, CELL, 41:521–530 (1985)), the SV40 promoter, the dihydrofolate reductase promoter, the β-actin promoter, the phosphoglycerol kinase (PGK) promoter, and the EF1α promoter (Invitrogen).

Inducible promoters are regulated by exogenously supplied compounds, including, the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, PROC. NATL. ACAD. SCI. USA, 93:3346–3351 (1996)), the tetracycline-repressible system (Gossen et al, PROC. NATL. ACAD. SCI. USA, 89:5547–5551 (1992)), the tetracycline-inducible system (Gossen et al, SCIENCE, 268:1766–1769 (1995); see also Harvey et al. CURR. OPIN. CHEM. BIOL., 2:512–518 (1998)), the RU486-inducible system (Wang et al, NAT. BIOTECH., 15:239–243 (1997) and Wang et al, GENE THER., 4:432–441 (1997)) and the rapamycin-inducible system (Magari et al, J. CLIN. INVEST., 100: 2865–2872 (1997)). Other types of inducible promoters which may be useful in the transgenes and other constructs described herein are those which are regulated by a specific physiological state, e.g., temperature, acute phase, a particular differentiation state of the cell, or in replicating cells only.

In another embodiment, the native promoter for the selected gene product will be used. The native promoter may be preferred when it is desired that expression of the product should mimic the native expression. The native promoter may be used when expression of the product must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In another embodiment, the sequences encoding a product to be expressed is operably linked to a tissue-specific promoter. For instance, if expression in skeletal muscle is desired, a promoter active in muscle should be used. These include the promoters from genes encoding skeletal α-actin, myosin light chain 2A, dystrophin, muscle creatine kinase, as well as synthetic muscle promoters with activities higher than naturally-occurring promoters (see Li et al., NAT. BIOTECH., 17:241–245 (1999)). Examples of promoters that are tissue-specific are known for liver (albumin, Miyatake et al. J. VIROL., 71:5124–32 (1997); hepatitis B virus core promoter, Sandig et al., GENE THER., 3:1002-9 (1996); and alpha-fetoprotein (AFP), Arbuthnot et al., HUM. GENE THER., 7:1503–14 (1996)), bone (osteocalcin, Stein et al., MOL. BIOL. REP., 24:185–96 (1997); and bone sialoprotein, Chen et al., J. BONE MINER. RES., 11:654–64 (1996)), lymphocytes (CD2, Hansal et al., J. IMMUNOL., 161:1063–8 (1998); immunoglobulin heavy chain; T cell receptor α chain), neuronal (neuron-specific enolase (NSE) promoter, Andersen et al. CELL. MOL. NEUROBIOL., 13:503–15 (1993); neurofilament light-chain gene, Piccioli et al., PROC. NATL. ACAD. SCI. USA, 88:5611–5 (1991); and the neuron-specific vgf gene, Piccioli et al., NEURON, 15:373–84 (1995)); among others.

Of course, not all expression control sequences will function equally well to express all of the products useful in this invention. However, one of skill in the art may make a selection among these expression control sequences without departing from the scope of this invention. Suitable promoter/enhancer sequences may be selected by one of skill in the art using the guidance provided by this application. Such selection is a routine matter and is not a limitation of the transgene or other construct. For instance, one may select one or more expression control sequences operably linked to the coding sequence of interest for use in a transgene for insertion in a "minigene" which is composed of the 5' ITRs, a transgene, and 3' ITRs. Such a minigene may have a size in the range of several hundred base pairs up to about 30 kb.

Thus, this system permits a great deal of latitude in the selection of the various components of the minigene, particularly the selected transgene, with regard to size. Provided with the teachings of this invention, the design of such a minigene can be made by resort to conventional techniques.

After following one of the methods for packaging the minigene taught in this specification, or as taught in the art, one may infect suitable cells in vitro or in vivo. Where the heterologous molecule comprises a transgene, the number of copies of the transgene in the cell may be monitored by Southern blotting or quantitative polymerase chain reaction (PCR). The level of RNA expression may be monitored by Northern blotting or quantitative reverse transcriptase (RT)-PCR. The level of protein expression may be monitored by Western blotting, immunohistochemistry, ELISA, RIA, or tests of the transgene's encoded product's biological activity. Thus, one may easily assay whether a particular expression control sequence is suitable for a specific transgene, and choose the expression control sequence most appropriate for expression of the desired transgene. Suitable methods for detecting the presence of other heterologous molecules delivered via the rAAV of the invention are known to those of skill in the art and are not a limitation of the present invention.

B. AAV Capsid

In a particularly preferred embodiment, the present invention provides a pseudotyped rAAV in which a non-AAV5 minigene is packaged in an AAV5 capsid or an AAV5 transfer vector is packaged in a non-AAV5 capsid. Suitably, the sequences providing the AAV capsid protein of the selected serotype may be obtained from any suitable source, as with the other AAV sequences described herein.

In still another embodiment, the invention provides a rAAV virus, in which both the AAV ITRs and capsid protein are of serotype 5. In this embodiment, the virus preferably contains modified 5' and/or 3' ITRs. More particularly, the virus desirably contains a 175-bp 5' ITR and a 182-bp 3' ITR. Desirably, in this embodiment, the rAAV5 virus further contains a promoter and an intron upstream of the transgene, and a woodchuck hepatitis virus post-transcriptional element and a bovine growth hormone polyA signal downstream of the transgene.

The rAAV of the invention, composed of AAV transfer vectors packaged in AAV capsid described herein, may be produced utilizing the following methods or other suitable methods known in the art.

II. Production of rAAV

The present invention provides a method which permits the production of a pseudotyped AAV virus, in which an AAV5 minigene is packaged in a heterologous AAV serotype capsid or in which a non-AAV5 serotype minigene is packaged in an AAV5 capsid. The inventors have found that this pseudotyping can be achieved by utilizing a rep protein (or a functional portion thereof) of the same serotype or a cross-reactive serotype as that of the ITRs found in the minigene in the presence of sufficient helper functions to permit packaging. Thus, an AAV2 minigene can be pseudotyped in an AAV5 capsid by use of a rep protein from AAV2 or a cross-reactive serotype, e.g., AAV1, AAV3, AAV4 or AAV6. Similarly, an AAV minigene containing AAV1 5' ITRs and AAV2 3' ITRs may be pseudotyped in an AAV5 capsid by use of a rep protein from AAV1, AAV2, or another cross-reactive serotype. However, because AAV5 is not cross-reactive with the other AAV serotypes, an AAV5 minigene can be pseudotyped in a heterologous AAV capsid only by use of an AAV5 rep protein.

Thus, in one embodiment, the invention provides a method of pseudotyping an AAV minigene in an AAV serotype 5 capsid. The method involves culturing in a host cell an AAV minigene containing ITRs which are derived from one or more serotypes heterologous to AAV5, a nucleic acid sequence driving expression of the AAV5 capsid protein, and a functional portion of an AAV rep of the same (or a cross-reactive) serotype as that of the AAV ITRs, in the presence of sufficient helper functions to permit packaging of the minigene in the AAV5 capsid.

In another embodiment, the invention provides a method of pseudotyping an AAV5 minigene in an AAV capsid from another serotype. The method involves culturing in a host cell an AAV minigene containing AAV5 ITRs, a nucleic acid sequence driving expression of the AAV capsid protein, and a functional portion of an AAV5 rep, in the presence of sufficient helper functions to permit packaging of the AAV ITR-heterologous molecule-AAV ITR minigene in the AAV capsid.

In still another embodiment, the invention provides a helper virus-free method of producing rAAV5 virus, in which both the AAV ITRs and capsid proteins are of serotype 5. In this embodiment, the virus preferably contains modified 5' and/or 3' ITRs.

In yet a further embodiment, the rAAV of the invention may be produced by in vitro packaging. In this embodiment, the capsid proteins are produced in host cells and extracted from the host cells, using production and purification techniques similar to those described for packaging of the rAAV in host cells. The extracted capsid proteins are then utilized for in vitro packaging of the virus. Suitable techniques for in vitro packaging are known to those of skill in the art. See, e.g., X. Zhou and N. Muzyczka, J. VIROL. 72:3341–3347 (April 1998). Selection of the appropriate packaging method for the rAAV of the invention is not a limitation of the present invention.

A. Delivery of Required Components to Packaging Host Cell

The components required to be cultured in the host cell to package the AAV minigene in the AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing the rAAV of the invention may be delivered to the packaging host cell in the form of any genetic element, e.g., naked DNA, a plasmid, phage, transposon, cosmid, virus, etc. which transfer the sequences carried thereon. The selected genetic element may be delivered by any suitable method, including transfection, electroporation, liposome delivery, membrane fusion techniques, high velocity DNA-coated pellets, viral infection and protoplast fusion.

The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y.

1. Delivery of Minigene

Currently, the minigene is preferably carried on a plasmid which is delivered to a host cell by transfection. The plasmids useful in this invention may be engineered such that they are suitable for replication and, optionally, integration in prokaryotic cells, mammalian cells, or both. These plasmids (or other vectors carrying the 5' AAV ITR-heterologous molecule-3'ITR) contain sequences permitting replication of the minigene in eukaryotes and/or prokaryotes and selection markers for these systems. Selectable markers or reporter genes may include sequences encoding geneticin, hygromicin or purimycin resistance, among others. The plasmids may also contain certain selectable reporters or marker genes that can be used to signal the presence of the vector in bacterial cells, such as ampicillin resistance. Other components of the plasmid may include an origin of replication and an amplicon, such as the amplicon system employing the Epstein Barr virus nuclear antigen. This amplicon system, or other similar amplicon components permit high copy episomal replication in the cells. Preferably, the molecule carrying the minigene is transfected into the cell, where it may exist transiently or preferably as an episome. Alternatively, the minigene (carrying the 5' AAV ITR-heterologous molecule-3' ITR) may be stably integrated into a chromosome of the host cell. Suitable transfection techniques are known and may readily be utilized to deliver the minigene to the host cell.

Generally, when delivering the vector comprising the minigene by transfection, the vector is delivered in an amount from about 5 μg to about 100 μg DNA, and preferably about 10 to about 50 μg DNA to about $1 \times 10^4$ cells to about $1 \times 10^{13}$ cells, and preferably about $10^5$ cells. However, the relative amounts of vector DNA to host cells may be adjusted, taking into consideration such factors as the selected vector, the delivery method and the host cells selected.

2. Rep and Cap Sequences

In addition to the minigene, the host cell must also contain the sequences which drive expression of the capsid protein of the selected AAV serotype in the host cell and rep sequences of the same serotype as the serotype of the AAV ITRs found in the minigene. The AAV cap and rep sequences may be independently obtained from an AAV source as described above and may be introduced into the host cell in any manner known to one in the art as described above. Additionally, when pseudotyping an AAV vector in an AAV5 capsid, the sequences encoding each of the essential rep proteins may be supplied by the same AAV serotype, or the sequences encoding the rep proteins may be supplied by different, but cross-reactive, AAV serotypes (e.g., AAV1, AAV2, AAV3, AAV4 and AAV6). For example, the rep78/68 sequences may be from AAV2, whereas the rep52/40 sequences may from AAV 1.

In one embodiment, the host cell stably contains the capsid protein under the control of a suitable promoter, such as those described above. Most desirably, in this embodiment, the capsid protein is expressed under the control of an inducible promoter. In another embodiment, the capsid protein is supplied to the host cell in trans. When delivered to the host cell in trans, the capsid protein may be delivered via a plasmid which contains the sequences necessary to direct expression of the selected capsid protein in the host cell. Most desirably, when delivered to the host cell in trans, the plasmid carrying the capsid protein also carries other sequences required for packaging the rAAV. e.g., the rep sequences.

In another embodiment, the host cell stably contains the rep sequences under the control of a suitable promoter, such as those described above. Most desirably, in this embodiment, the essential rep proteins are expressed under the control of an inducible promoter. In another embodiment, the rep proteins are supplied to the host cell in trans. When delivered to the host cell in trans, the rep proteins may be delivered via a plasmid which contains the sequences necessary to direct expression of the selected rep proteins in the host cell. Most desirably, when delivered to the host cell in trans, the plasmid carrying the capsid protein also carries other sequences required for packaging the rAAV, e.g., the rep and cap sequences.

Thus, in one embodiment, the rep and cap sequences may be transfected into the host cell on a single nucleic acid molecule and exist stably in the cell as an episome. In another embodiment, the rep and cap sequences are stably integrated into the genome of the cell. Another embodiment has the rep and cap sequences transiently expressed in the host cell. For example, a useful nucleic acid molecule for such transfection comprises, from 5' to 3', a promoter, an optional spacer interposed between the promoter and the start site of the rep gene sequence, an AAV rep gene sequence, and an AAV cap gene sequence.

Optionally, the rep and/or cap sequences may be supplied on a vector that contains other DNA sequences that are to be introduced into the host cells. For instance, the vector may contain the rAAV construct comprising the minigene. The vector may comprise one or more of the genes encoding the helper functions, e.g., the adenoviral proteins E1, E2a, and E4ORF6, and the gene for VAI RNA.

Preferably, the promoter used in this construct may be any of the constitutive, inducible or native promoters known to one of skill in the art or as discussed above. In one embodiment, an AAV P5 promoter sequence is employed. The selection of the AAV to provide any of these sequences does not limit the invention.

In another preferred embodiment, the promoter for rep is an inducible promoter, as are discussed above in connection with the transgene regulatory elements. One preferred promoter for rep expression is the T7 promoter. The vector comprising the rep gene regulated by the T7 promoter and the cap gene, is transfected or transformed into a cell which either constitutively or inducibly expresses the T7 polymerase. See WO 98/10088, published Mar. 12, 1998.

The spacer is an optional element in the design of the vector. The spacer is a DNA sequence interposed between the promoter and the rep gene ATG start site. The spacer may have any desired design; that is, it may be a random sequence of nucleotides, or alternatively, it may encode a gene product, such as a marker gene. The spacer may contain genes which typically incorporate start/stop and polyA sites. The spacer may be a non-coding DNA sequence from a prokaryote or eukaryote, a repetitive non-coding sequence, a coding sequence without transcriptional controls or a coding sequence with transcriptional controls. Two exemplary sources of spacer sequences are the λ phage ladder sequences or yeast ladder sequences, which are available commercially, e.g., from Gibco or Invitrogen, among others. The spacer may be of any size sufficient to reduce expression of the rep78 and rep68 gene products, leaving the rep52, rep40 and cap gene products expressed at normal levels. The length of the spacer may therefore range from about 10 bp to about 10.0 kbp, preferably in the range of about 100 bp to about 8.0 kbp. To reduce the possibility of recombination, the spacer is preferably less than 2 kbp in length; however, the invention is not so limited.

Although the molecule(s) providing rep and cap may exist in the host cell transiently (i.e., through transfection), it is preferred that one or both of the rep and cap proteins and the promoter(s) controlling their expression be stably expressed in the host cell, e.g., as an episome or by integration into the chromosome of the host cell. The methods employed for constructing embodiments of this invention are conventional genetic engineering or recombinant engineering techniques such as those described in the references above. While this specification provides illustrative examples of specific constructs, using the information provided herein, one of skill in the art may select and design other suitable constructs, using a choice of spacers, P5 promoters, and other elements, including at least one translational start and stop signal, and the optional addition of polyadenylation sites.

In another embodiment of this invention, the rep or cap protein may be provided stably by a host cell.

3. The Helper Functions

The packaging host cell also requires helper functions in order to package the rAAV of the invention. Optionally, these functions may be supplied by a herpesvirus. Most desirably, the necessary helper functions are provided from an adenovirus source. In one currently preferred embodiment, the host cell is provided with and/or contains an E1a gene product, an E1b gene product, an E2a gene product, and/or an E4 ORF6 gene product. The host cell may contain other adenoviral genes such as VAI RNA, but these genes are not required. In a preferred embodiment, no other adenovirus genes or gene functions are present in the host cell.

The DNA sequences encoding the adenovirus E4 ORF6 genes and the E1 genes and/or E2a genes useful in this invention may be selected from among any known adenovirus type, including the presently identified 46 human types [see, e.g., Horwitz, cited above and American Type Culture Collection]. Similarly, adenoviruses known to infect other animals may supply the gene sequences. The selection of the adenovirus type for each E1, E2a, and E4 ORF6 gene sequence does not limit this invention. The sequences for a number of adenovirus serotypes, including that of serotype Ad5, are available from Genbank. A variety of adenovirus strains are available from the American Type Culture Collection (ATCC), Manassas, Va., or are available by request from a variety of commercial and institutional sources. Any one or more of human adenoviruses Types 1 to 46 may supply any of the adenoviral sequences, including E1, E2a, and/or E4 ORF6.

By "adenoviral DNA which expresses the E1a gene product", it is meant any adenovirus sequence encoding E1a or any functional E1a portion. Adenoviral DNA which expresses the E2a gene product and adenoviral DNA which expresses the E4 ORF6 gene products are defined similarly. Also included are any alleles or other modifications of the adenoviral gene or functional portion thereof. Such modifications may be deliberately introduced by resort to conventional genetic engineering or mutagenic techniques to enhance the adenoviral function in some manner, as well as naturally occurring allelic variants thereof. Such modifications and methods for manipulating DNA to achieve these adenovirus gene functions are known to those of skill in the art.

The adenovirus E1a, E1b, E2a, and/or E4ORF6 gene products, as well as any other desired helper functions, can be provided using any means that allows their expression in a cell. Each of the sequences encoding these products may be on a separate vector, or one or more genes may be on the same vector. The vector may be any vector known in the art or disclosed above, including plasmids, cosmids and viruses. Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously-added factors, for example.

B. Host Cells And Packaging Cell Lines

The host cell itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, 293 cells (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The requirements for the cell used is that it not carry any adenovirus gene other than E1, E2a and/or E4 ORF6; it not contain any other virus gene which could result in homologous recombination of a contaminating virus during the production of rAAV; and it is capable of infection or transfection of DNA and expression of the transfected DNA. In a preferred embodiment, the host cell is one that has rep and cap stably transfected in the cell.

One host cell useful in the present invention is a host cell stably transformed with the sequences encoding rep and cap, and which is transfected with the adenovirus E1, E2a, and E4ORF6 DNA and a construct carrying the minigene as described above. Stable rep and/or cap expressing cell lines, such as B-50 (PCT/US98/19463), or those described in U.S. Pat. No. 5,658,785, may also be similarly employed. Another desirable host cell contains the minimum adenoviral DNA which is sufficient to express E4 ORF6.

The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods which provide the desired nucleotide sequence.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins).

III. Pharmaceutical Compositions

The rAAV according to the present invention are suitable for a variety of uses including in vitro protein and peptide expression, as well as ex vivo and in vivo gene delivery.

The rAAV of the invention may be used to deliver a selected molecule to a host cell by any suitable means. In one embodiment, the rAAV and the cells are mixed ex vivo; the infected cells are cultured using conventional methodologies; and the transduced cells are re-infused into the patient.

Alternatively, the rAAV, preferably suspended in a physiologically compatible carrier, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

In one embodiment, rAAV of the invention are suitable for applications in which transient transgene expression or delivery of another selected molecule is therapeutic (e.g., p53 gene transfer in cancer and VEGF gene transfer in heart diseases). However, the rAAV are not limited to use where transient transgene expression is desired. The rAAV are useful for a variety of situations in which delivery and expression of a selected molecule is desired.

Thus, the rAAV of the invention, are useful for any of a variety of delivery applications. Significantly, the rAAV5 of the invention provide advantages over prior art viruses, in that the rAAV5 of the invention lack serological cross-activity with rAAV of other serotypes.

IV. Methods of Delivering Genes Via Pseudotyped rAAV Containing AAV5 Sequences or Protein In another aspect, the present invention provides a method for delivery of a heterologous molecule (e.g., a transgene product) to a host which involves infecting a selected host cell with a rAAV of the invention. Methods for delivery are well known to those of skill in the art and are not a limitation of the present invention.

In one desirable embodiment, the invention provides a method for AAV-mediated delivery of a transgene to a host. This method involves a selected host cell with a rAAV containing a selected transgene under the control of sequences which direct expression thereof and AAV5 capsid proteins. This embodiment is particularly desirable, because AAV5 capsids are not recognized by neutralizing antibodies to other AAV serotypes.

In another embodiment, the invention provides a method of infecting a selected host cell with a rAAV containing a AAV5 transfer vector packaged in a capsid protein of another AAV serotype. Optionally, a sample from the host may be first assayed for the presence of antibodies to a selected AAV serotype. A variety of assay formats for detecting neutralizing antibodies are well known to those of skill in the art. The selection of such an assay is not a limitation of the present invention. See, e.g., Fisher et al, NATURE MED., 3(3):306–312 (March 1997) and W. C. Manning et al, HUMAN GENE THERAPY, 9:477–485 (Mar. 1, 1998). The results of this assay may be used to determine from which serotype the capsid protein will be preferred for delivery, e.g., by the absence of neutralizing antibodies specific for that capsid serotype.

In another embodiment of this method, the delivery of vector with an AAV5 capsid protein may precede or follow delivery of a heterologous molecule (e.g., gene) via a vector with a different serotype AAV capsid protein. Thus, delivery via multiple rAAV vectors may be used for repeat delivery of a desired molecule to a selected host cell. Desirably, subsequently administered rAAV carry the same minigene as the first rAAV vector, but the subsequently administered vectors contain capsid proteins of serotypes which differ from the first vector. For example, if a first rAAV has an AAV5 capsid protein, subsequently administered rAAV may have capsid proteins selected from among the other serotypes, including AAV2, AAV1, AAV3A, AAV3B, AAV4 and AAV6. Alternatively, if a first rAAV has an AAV2 capsid protein, subsequently administered rAAV may have an AAV5 capsid.

Thus, AAV5-derived rAAV of the invention provide efficient transfer vehicles which can deliver a selected heterologous molecule to a selected host cell in vivo or ex vivo even where the organism has neutralizing antibodies to one or more AAV serotypes. These compositions are particularly well suited to delivery of molecules for therapeutic purposes. However, the compositions of the invention may also be useful in immunization by delivery of immunogenic or antigenic molecules. Further, the compositions of the invention may also be used for production of a desired product in vitro.

The above-described rAAV may be delivered to host cells according to published methods. A rAAV bearing the selected heterologous molecule may be administered to a human or veterinary patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The rAAV are administered in sufficient amounts to transduce the cells and to provide sufficient transfer levels of genes (or other molecules) and expression to provide a medical benefit without undue adverse effects, or with medically acceptable physiological effects, which can be determined by those skilled in the medical arts. Conventional and pharmaceutically acceptable routes of administration include, but are not limited to, direct delivery to the liver, intranasal, intravenous, intramuscular, subcutaneous, intradermal, oral and other parental routes of administration. Routes of administration may be combined, if desired.

Dosages of the rAAV will depend primarily on factors such as the condition being treated, the age, weight and health of the patient, and may thus vary among patients. For example, a therapeutically effective human dosage of the rAAV is generally in the range of from about 1 ml to 100 ml, 5 to 50 ml, or 10 to 25 ml of saline solution containing concentrations of from about $1 \times 10^9$ to $1 \times 10^{16}$ genomes rAAV/ml, preferably about $10^{13}$ to $10^{15}$ genomes rAAV/ml virus vector. A preferred human dosage may be about $1 \times 10^{13}$ AAV genomes rAAV/ml. The dosage will be adjusted to balance the therapeutic benefit against any side effects. Such dosages may vary depending upon the therapeutic application for which the recombinant vector is employed. The levels of expression of the transgene can be monitored to determine the frequency of dosage of viral vectors, preferably AAV vectors, containing the minigene. Optionally, dosage regimens similar to those described for therapeutic purposes may be utilized for immunization using the compositions of the invention.

For in vitro production, a desired product (e.g., a protein) may be obtained from a desired culture following transfection of host cells with a rAAV containing the molecule encoding the desired product and culturing the cell culture under conditions which permit expression. The expressed product may then be purified and isolated, as desired. Suitable techniques for transfection, cell culturing, purification, and isolation are known to those of skill in the art.

The following examples illustrate several aspects and embodiments of the invention.

EXAMPLE 1

Pseudotyping of AAV2 Transfer Vector in AAV Capsid

A. pAAV2.1lacZ

The AAV2 plasmid which contains the AAV2 ITRs and the beta-galactosidase gene of *E. coli* with the cytomegalovirus (CMV) promoter was constructed as described below. Plasmid pAAV2.1lacZ contains 6 elements:

(i) Plasmid Backbone pAAV2.1 Containing the AAV2 ITRs:

A pUC-19 based expression plasmid (pZAC3.1) was digested with the restriction enzymes BglII and ClaI and the cohesive ends filled in using Pfu Polymerase (Stratagene). Afterwards, an EcoRI linker (New England Biolabs) was introduced. After EcoRI digestion, the construct was religated, resulting in plasmid pAAV2.1, which provides the plasmid backbone containing the AAV2 5' ITRs and AAV2 3' ITRs.

(ii) CMV Promoter:

The CMV promoter was amplified with Pfu Polymerase with pEGFP-C1 (Clontech) as template using primers:

```
CLONE/CMV promoter/NheI+:
AAGCTAGCTAGTTATTAATAGTAATC:        SEQ ID NO:1

CLONE/CMV promoter/PstI-:
AACTGCAGGATCTGACGGTTCACTAAAC:      SEQ ID NO:2
``` and ligated into pCR4topo (Invitrogen). The CMV promoter fragment was cut out with EcoRI and PstI, so that an EcoRI site flanks the NheI site.

(iii) Chimeric Intron:

The chimeric intron was amplified with Pfu Polymerase with pCI (Promega) as template using primers:

```
CLONE/SV40 intron/Pst+:
AACTGCAGAAGTTGGTCGTGAGGCAC:        SEQ ID NO:3

CLONE/SV40 intron/NotI-:
AAGCGGCCGCCTGGACACCTGTGGAGAAAG:    SEQ ID NO:4
``` and afterwards digested with the restriction enzymes PstI and NotI, resulting in the chimeric intron fragment.

(iv) Beta-galactosidase Coding Sequence:

The beta-galactosidase coding sequence was amplified with Pfu Polymerase (Stratagene) with *E. coli* genomic DNA (ATCC) as template using primers:

```
CLONE/lacZ/NotI+:
AAGCGGCCGCCATGACCATGATTACGGATTC:   SEQ ID NO:5

CLONE/lacZ/BamHI-:
TTGGATCCTTATTTTTGACACCAGAC:        SEQ ID NO:6
``` and afterwards digested with the restriction enzymes NotI and BamHI resulting in the beta-galactosidase fragment.

(v) Woodchuck Hepatitis Post-regulatory Element (WPRE):

The WPRE element was amplified with Pfu Polymerase with woodchuck hepatitis virus DNA (ATCC) as template using primers:

```
CLONE/WPRE/BamHI+:
AAGGATCCAATCAACCTCTGGATTAC:        SEQ ID NO:7

CLONE/WRPRE/BglII-:
TTAGATCTCGAAGACGCGGAAGAGGCCG:      SEQ ID NO:8
``` and afterwards digested with the restriction enzymes BamHI and BglII resulting in the WPRE fragment.

(vi) Bovine Growth Hormone Polyadenylation Signal:

The bovine growth hormone polyadenylation signal (BGHpA) was amplified with Pfu Polymerase with pCDNA3.1 (Invitrogen) as template using primers:

```
CLONE/BGH pA/BglII+:
TTTAGATCTGCCTCGACTGTGCCTTCTAG:     SEQ ID NO:9

CLONE/BGH pA/XhoI-:
AACTCGAGTCCCCAGCATGCCTGCTATTG:     SEQ ID NO:10
``` and ligated into pCR4 topo (Invitrogen). The BGHpA fragment was excised with BglII and EcoRI so that EcoRI flanks the XhoI site.

In order to assemble pAAV2.1lacZ, the plasmid pAAV2.1 was cut with EcoRI and ligated together with the CMV promoter fragment (EcoRI/PstI), chimeric intron fragment (PstI/NotI), beta-galactosidase coding sequence (NotI/BamHI), WPRE element (BamHI/BglII), BGHpA fragment (BglII/EcoRI) in a multi-fragment ligation resulting in plasmid pAAV2.1 lacZ.

B. Cloning of p600 Trans

The P5 promoter was excised from pCR-p5 by BamHI and XhoI, filled in by Klenow and then cloned into pMMTV-Trans at SmaI+ClaI to obtain pP5-X-Trans. The construction of pCR-p5 and pMMTV-Trans were described previously (Xiao et al, J. VIROL, 73:3994–4003 (1999)). There is a unique EcoRV site between the P5 promoter and the initiation codon of Rep78 in pP5-X-Trans. All helper plasmids are made by cloning either the 100 bp ladder or 500 bp ladder from Gibco BRL using the EcoRV site in p5-X-Trans. These series of plasmids are designated as pSY, where Y indicates the size of the spacer which ranges from 100 bp to 5 kb. Thus, the p600trans plasmid contains a 600 bp insert consisting of the 500 bp ladder and a 100 bp spacer.

Plasmid p600trans (containing the rep and cap proteins of AAV serotype 2) was subjected to PCR amplification with Pfu Polymerase (Stratagene) according to manufacturer's instructions (Seemless cloning kit) using primers:

```
Clone/AAV2rep.cap seemless+:
                                   SEQ ID NO:11
AGTTACTCTTCTTGCTTGTTAATCAATAAACCGTTTAATTCG:

Clone/AAV2rep.cap seemless-:
                                   SEQ ID NO:12
AGTTACTCTTCACCTGATTTAAATCATTTATTGTTCAAAGATGC.
```

Following PCR, the plasmid was digested with restriction enzyme Eam 1104 I, to provide fragment p600 trans ΔCAP-ORF. This fragment contains the sequences encoding AAV2 rep proteins 78 and 52. The AAV2 Rep68 and Rep40 proteins have a amino acid deletion as compared to the wt AAV Rep68 and Rep 40. In addition the last five C-terminal amino acids are substituted (i.e., sAA, sAA, sAA, sAA, dAA, dAA, with s: substituted, d: deleted), because of the overlap between their C-termini and the AAV5 VPI open reading frame.

AAV5-CAP-ORF (U. Bantel-Schaal, J. VIROL., 73/2: 939–947 (February 1999)) was amplified by PCR with Pfu Polymerase as above, using the primers:

Clone/AAV5 Cap seemless+: SEQ ID NO:13:

AGTTACTCTTCCAGGTATGTCTTTTGT-TGATCACCCTCCAGATTGG

Clone/AAV5 CAP seemless-: SEQ ID NO:14:

AGTTACTCTTCAGCAAT-TAAAGGGGTCGGGTAAGGTATCGGGTTC and thereafter digested with Eam 1104I, to provide AAV5-CAP5. This fragment contains the sequences encoding the AAV5 capsid protein.

The fragments resulting from the above described PCR amplifications, p600 trans ΔCAP-ORF and AAV5-CAP5, were ligated according to manufacturer's instructions. The resulting plasmid contains the AAV2 rep sequences for Rep78/68 under the control of the AAV2 P5 promoter, and the AAV2 rep sequences for Rep52/40 under the control of the AAV2 P 19 promoter. The AAV5 capsid sequences are under the control of the AAV2 P40 promoter, which is located within the Rep sequences. This plasmid further contains a spacer 5' of the rep ORF.

C. Production of Pseudotyped rAAV

The rAAV particles (AAV2 vector in AAV5 capsid) were generated using an adenovirus-free method. Briefly, the cis plasmid (pAAV2.1 lacZ plasmid containing AAV2 ITRs), and the trans plasmid pAdΔF6 (containing the AAV2 rep and AAV5 cap) and a helper plasmid, respectively, were simultaneously co-transfected into 293 cells in a ratio of 1:1:2 by calcium phosphate precipitation.

For the construction of the pAd helper plasmids, pBG10 plasmid was purchased from Microbix (Canada). A RsrII fragment containing L2 and L3 was deleted from pBHG10, resulting in the first helper plasmid, pAdΔF13. Plasmid AdΔF1 was constructed by cloning Asp700/SalI fragment with a PmeI/SgfI deletion, isolating from pBHG 10, into Bluescript. MLP, L2, L2 and L3 were deleted in the pAdΔF1. Further deletions of a 2.3 kb NruI fragment and, subsequently, a 0.5 kb RsrII/NruI fragment generated helper plasmids pAdΔF5 and pAdΔF6, respectively. The helper plasmid, termed pΔF6, provides the essential helper functions of E2a and E4 ORF6 not provided by the E1-expressing helper cell, but is deleted of adenoviral capsid proteins and functional E1 regions).

Typically, 50 μg of DNA (cis:trans:helper) was transfected onto a 15 cm tissue culture dish. The 293 cells were harvested 72 hours post-transfection, sonicated and treated with 0.5% sodium deoxycholate (37° C. for 10 min.) Cell lysates were then subjected to two rounds of a CsCl gradient. Peak fractions containing rAAV vector are collected, pooled and dialyzed against PBS.

EXAMPLE 2

Production of rAAV5

A. pAAV5.1LacZ

The AAV5 plasmid which contains the modified AAV5 ITRs and the nucleus-localized beta-galactosidase gene with a cytomegalovirus (CMV) promoter was constructed as described below.

The plasmid, pAAVRnLacZ (J. A. Chiorini et al, HUM. GENE THER., 6:1531–1541 (1995)), was subjected to PCR amplification with Pfu Polymerase (Stratagene), according to manufacturer's instructions using the primers shown below, to provide plasmid pAAV5.1.

Clone/AAV5/NheI-XhoI:
SEQ ID NO:15
AAACTCGAGATTGCTAGCTCACTGCTTACAAAACCCCCTTGCTTGAG:

Clone/AAV5/XhoI+:
SEQ ID NO:16
TTCACAGCTTACAACATCTACAAAAC:

pAAV5.1 was digested with pAAV5.1 with restriction enzymes NheI and XhoI and the NheI/XhoI fragment containing the lacZ expression cassette of pAAV2.1lacZ (described above) was inserted, resulting in the plasmid pAAV5.1acZ B. Construction of pAAV5.1eGFP eGFP was amplified with Pfu Polymerase (Stratagene) according to manufacturer's instructions using pEGFP-C1 (Clontech) as template with the primers:

CLONE/eGFP/NotI+:
SEQ ID NO:17
AAAGCGGCCGCCATGGTGAGCAAGGGCGAGGAG:

CLONE/eGFP/HindIII-BamHI-:
SEQ ID NO:18
AAGGATCCAAGCTTATTACTTGTACAGCTCGTCCATGCC:

and digested with the restriction enzymes NotI and BamHI resulting in the fragment eGFP. This fragment was ligated into pAAV5.1lacZ in which the lacZ coding sequence was removed by digestion with NotI and BamHI resulting in the plasmid pAAV5.1 eGFP.

C. Transduction Efficiency of rAAV with AAV5 Capsids

These rAAV were injected ($1 \times 10^{10}$ to $4 \times 10^{10}$ genomes) into murine lung, liver, intestine and muscle tissue with recombinant AAV2 as a control vector. Preliminary results suggest a higher transduction efficiency of lung, intestine and muscle tissue by AAV5 than by AAV2. This indicates that vectors containing AAV5 capsids are extremely useful for targeting lungs, e.g., for the correction of the autosomal recessive inherited disease Cystic Fibrosis (CF) by delivery of the CFTR gene, and muscle.

EXAMPLE 3

Transduction Efficiency of Skeletal Muscle with rAAV2/5

Initial experiments evaluated expression of CMV-lacZ in mouse skeletal muscle injected with equal quantities of AAV5 or AAV2/5 vectors. Transduction of murine muscle with AAV5 CMVlacZ was accomplished by injection of the right anterior tibialis of C57BL/6 mice with $10^{10}$ genome copies of AAV5 CMVlacZ and harvesting 28 days post-injection. Similarly, transduction of murine muscle with AAV2/5 CMVlacZ and AAV2 CMVlacZ respectively; was accomplished by injection of the right anterior tibialis muscle of C57BL/6 mice with $4 \times 10^{10}$ genome copies of AAV2/5 CMVlacZ and AAV2 CMVlacZ respectively. In these cases, muscles were harvested 60 days post-injection.

Histochemical analysis revealed equivalent lacZ expression between AAV5 and AAV2/5 which is higher than what was achieved with an AAV2 vector. These studies also revealed significantly higher yields of AAV5 as compared to AAV2/5. All subsequent studies were performed with AAV2/5 vectors.

The yield of AAV2/5 vector is essentially identical to AAV2 vector using standard transfection approaches. Table 1 summarizes vector yield based on genome copies for 7 vectors packaged with either AAV2 or AAV2/5 constructs. With reference to the table, GC refers to genome copies; CMV to cytomegalovirus promoter; TBG to tyroxine-binding globulin promoter; rhCG to rhesus chorionic gonadotropin; cFIX to canine factor IX; W to woodchuck hepatitis post-transcriptional regulatory element; mInsM to furin-modified mouse proinsulin; EGFP to enhanced green fluorescent protein. Average genome copies are calculated where >1 recombinant AAV prep has been produced.

TABLE 1

| Transgene Cassette | AAV2 | | AAV2/5 | |
| --- | --- | --- | --- | --- |
| | Lot # | Yield (GC) | Lot # | Yield (GC) |
| CMV LacZ2 | Z-438 | 2.60 ± 12 | Z-481 | 4.34 ± 12 |
| | Z-439 | 8.40 ± 12 | Z-483 | 4.65 ± 12 |
| | Z-441 | 9.00 ± 12 | Z-484 | 5.60 ± 12 |
| | Z-460 | 5.25 ± 12 | Z-485 | 4.96 ± 12 |
| | Z-479 | 5.20 ± 12 | Z-502 | 7.50 ± 12 |
| | Z-496 | 8.96 ± 12 | | |
| | Average | 6.57 ± 12 | Average | 5.41 ± 12 |
| CMV rhCG | Z-434 | 5.98 ± 12 | Z-487 | 9.60 ± 12 |
| | Z-495 | 1.87 ± 13 | Z-492 | 1.65 ± 13 |
| | | | Z-500 | 9.36 ± 12 |
| | Average | 1.23 ± 13 | Average | 9.75 ± 12 |
| TBG rhCG | Z-471 | 2.30 ± 13 | Z-489 | 1.40 ± 13 |
| | Z-475 | 1.40 ± 12 | Z-490 | 1.62 ± 13 |
| | | | Z-491 | 1.24 ± 13 |
| | Average | 1.33 ± 13 | Average | 1.41 ± 13 |
| TBG cFIX W | Z-331 | 2.10 ± 12 | Z-473 | 1.50 ± 13 |
| | Z-332 | 4.00 ± 12 | | |
| | Z-337 | 7.04 ± 12 | | |
| | Z-338 | 6.60 ± 12 | | |
| | Z-344 | 2.20 ± 12 | | |
| | Z-345 | 3.12 ± 12 | | |
| | Z-348 | 1.50 ± 13 | | |
| | Z-371 | 1.20 ± 13 | | |
| | Average | 6.51 ± 12 | | |
| TBG LacZ3 | Z-398 | 2.30 ± 12 | Z-472 | 4.00 ± 12 |
| | Z-401 | 1.04 ± 12 | | |
| | Z-505 | 3.50 ± 12 | | |
| | Average | 2.28 ± 12 | | |
| CMV mInsM | AA70 | 2.00 ± 12 | AA79 | 2.50 ± 12 |
| CMV EGFP | AA45 | 1.50 ± 12 | AA74 | 2.20 ± 12 |

A quantitative analysis of lacZ expression from AAV2 or AAV2/5 vectors following injection into murine skeletal muscle revealed a 2-fold increase from the AAV2/5 vectors. Enzymatic analysis for β-galactosidase from tissue homogenates demonstrated 3.6±0.1 μg β-gal/g tissue for AAV2 and 7.3±1.2 μg β-gal/g for AAV2/5 (N=6,±1 S.D.). The difference in inherent biological activity of these vectors may be even greater since the AAV2 vector was purified by heparin chromatography while the AAV2/5 vector was purified by cesium chloride sedimentation, which diminishes vector potency by approximately 10-fold (A. Auricchio et al, HUM GENE THER, 12:71–76 (2001)).

EXAMPLE 4

Transduction Efficiency of Smooth Muscle with rAAV2/5

The ability of the pseudotyped AAV2/5 constructs to transduce smooth muscle cells was assessed using AAV2/5 CMVlacZ by injecting $10^{10}$ genome copies of AAV2/5 CMVlacZ subcutaneously in C57BL/6 mice. β-galactosidase expression was assessed 60 days after vector administration.

In addition, apical transduction of primary human epithelial airway cells was assessed with AAV2/5 CMVlacZ. Primary human airway epithelial cells were infected apically with $5 \times 10^{10}$ genomic particles of the corresponding virus (liquid-air transwell system). Cells were fixed and stained with x-gal seven days post-infection.

The AAV2/5 lacZ vector was evaluated in a number of other tissues. Subcutaneous injection of vector led to substantial lacZ expression in smooth muscle cells. AAV2/5 vector more efficiently infects differentiated airway epithelial cells from the apical surface than achieved with AAV2.

EXAMPLE 5

Influence of Neutralizing Antibodies on Vector Readministration

One advantage of AAV2/5 vectors is that they should be serologically distinct from AAV2 based on antibody neutralization. This may allow in vivo gene transfer in patients with preexisting immunity to AAV2 which represents approximately 25% of normal subjects (N. Chirmule, et al., GENE THERAPY, 6:1574–1583 (1999)) and may facilitate readministration with AAV2/5 following infusion with AAV2 vector.

To test for cross neutralization in vivo, experiments were conducted in immune competent mice injected intramuscularly with AAV2 or AAV2/5 eGFP vector followed 28 days later by intramuscular injection into the contralateral leg with AAV2 or AAV2/5 lacZ vector. β-gal expression was evaluated by enzymatic analysis of tissue homogenates harvested 14 days after the second injection.

A. Influence of Neutralizing Antibodies to AAV2 on Vector Readministration.

Immunocompetent mice (C57BL/6) were injected with $3 \times 10^{10}$ genome copies of AAV2 CMV eGFP into the right anterior tibialis muscle (K. Fisher et al, NAT. MED., 3:306–312 (1997)) and, 28 days later, were injected with $3 \times 10^{10}$ genome copies of either AAV2 CMVlacZ or AAV2/5 CMVlacZ into the left anterior tibialis muscle. β-galactosidase expression was determined 14 days after the second injection by ELISA (Boehringer Mannheim, Germany) according to manufacturer's instructions. Mean values of six animals per group are shown.

Immunization with AAV2 eGFP diminished the effectiveness of a subsequent administration of AAV2 lacZ by 20-fold, but had no effect on expression from an AAV2/5 vector (i.e., gene expression equivalent to that observed in naïve animals). (FIG. 1A)

B. Influence of Neutralizing Antibodies to AAV2/5 on Vector Readministration.

Immunocompetent mice (C57BL/6) were injected with $4 \times 10^{10}$ genome copies of AAV2/5 CMV eGEP into the right anterior tibialis muscle and—28 days later—injected with $10^{10}$ genome copies of either AAV2 CMVlacZ or AAV2/5 CMVlacZ into the left anterior tibialis muscle. (Note: The AAV2/5 CMVlacZ virus preparation in this experiment is different from the ones used for the previous experiments). β-galactosidase expression was determined 14 days after the second injection by ELISA (Boehringer Mannheim, Germany) according to manufacturer's instructions. Mean values of eight animals per group are shown.

The reverse experiment yielded identical results: immunization with AAV2/5 blocked AAV2/5 readministration but not AAV2 gene transfer and expression (FIG. 1B).

EXAMPLE 6

Prevalence of Neutralizing Antibodies to AAV in the Human Population

A cohort of 85 human volunteers, previously evaluated for neutralizing antibodies to AAV1 and AAV2 were evaluated for neutralizing antibodies to AAV2/5. Neutralizing antibody titers were determined as previously described (J. Bennett, et al, PROC NATL ACAD USA, 96: 9920–9925 (August 1999); N. Chirmule, et al., J. VIROL., 71:6823–6833 (1997))

with the modification of using AAV5 CMV eGFP 3 instead of an AAV2 eGFP virus for the measurement of AAV5 neutralizing antibodies.

Sera of 85 human volunteers were tested for the presence of neutralizing antibodies to AAV1, AAV2 and AAV5. All samples tested were negative for AAV5 neutralizing antibodies. Even sera with high neutralizing activity to AAV1 or AAV2 did not inhibit AAV5 infectivity. Nineteen percent (19%) of the volunteers screened had neutralizing antibodies to AAV1 and 26% had neutralizing antibodies to AAV2. No one of the 85 persons screened showed detectable levels of AAV5 neutralizing antibodies.

It was surprising to see that not a single subject demonstrated neutralizing antibodies to AAV2/5 despite the prevalence of neutralizing antibodies to AAV1 and AAV2 in 19 and 25% of subjects, respectively. The lack of neutralizing antibodies to AAV5 in our study contrasts with a previous study of AAV5 seroepidemiology performed (in 1984 by S. Geog-Fries et al, VIROL., 134(1):64–71 (1984)) using an ELISA assay which detected antibodies to AAV5 capsid proteins in 60% of individuals. Our experience with AAV2 suggests that ELISA is a more sensitive, and potentially less specific, assay for a specific serologic response; of 74 subjects analyzed, 96% were ELISA positive for AAV2, while only 32% were able to neutralize infection of AAV2 (N. Chirmule et al, GENE THERAPY, 6:1574–1583 (1999)). The absence of neutralizing antibodies to AAV2/5 is potentially important for human applications. In contrast to AAV2, where at least a quarter of all patients may have diminished engraftment of vector due to preexisting immunity, AAV2/5 uptake should not be affected by immune status in the context of primary vector administration.

EXAMPLE 6

In vivo Delivery of Therapeutic Proteins by AAV2/5 Vectors

In the present study, it was demonstrated that aerosolized AAV2/5 encoding a secretable protein results in levels of mice hematocrit as increased as if the same viral dose is injected intramuscularly or intradermally. Therefore, it is possible to conclude that intranasal administration is an efficient way to obtain therapeutic protein secretion in this bloodstream.

A. Vector Construction and Adeno-Associated Virus (AAV) 2/5 Purification

The hybrid 2/5 packaging construct was prepared as described above, by ligation of the fragment p600 ΔCAP and fragment AAV5-CAP.

Plasmid pAd-ΔF6 was prepared as described above. PAAV2.1-CMV-mEpo was constructed as follows: the mEpo coding sequence was cut NotI-HindIII from PCR2.1mEpo and cloned into pAAV2.1.CMV.LacZ cut in the same way.

B. Virus Production

All recombinant virus stocks were produced helper-virus free in the following way. 293 cells were triple-transfected with the corresponding cis plasmid, packaging construct and Ad helper pF6. For production of AAV2/5 hybrid vectors, the corresponding AAV2 cis plasmid was used. Cells were harvested 72 hours after transfection, and recombinant virus was purified by three rounds of $CsCl^2$ banding. Titers were determined by real-time PCR.

C. Animal studies

Five (5)-six week C57/BL6 mice were administered $1\times10^{11}$ genomic copies of AAV2/5 either intranasally or via an alternative route for comparison as indicated. Sixty days after vector administration transgene expression was assessed either by β-galactosidase staining or by hemacrit measurements.

When lacZ expression was assessed in murine lungs after intranasal administration, as described, lacZ positive cells were evident in the upper airway epithelial cells and in the lower airway. Positive cells were present at the level of a bronchiole's wall as well as at the interalveolar septum level.

Analysis of hematocrit levels of the mice revealed that aerosolized AAV2/5 encoding mouse erythropoietin results in levels of mice hematocrit as increased as if the same viral dose is injected intramuscularly or intradermally.

All publications cited in this specification are incorporated herein by reference. While the invention has been described with reference to particularly preferred embodiments, it will be appreciated that modifications can be made without departing from the spirit of the invention. Such modifications are intended to fall within the scope of the claims.

What is claimed is:

1. A method of delivering a heterologous molecule to a selected mammalian or veterinary patient, comprising:
    contacting the cells of the patient with a recombinant type 5 adeno-associated virus (rAAV5), said rAAV5 comprising:
        a minigene comprising AAV 5' ITRs, a heterologous nucleic acid molecule, wherein said nucleic acid molecule is a transgene comprising a nucleic acid sequence encoding a product which is under the control of regulatory sequences which direct expression of the product in a host cell, and AAV 3' ITRs;
        an AAV5 capsid in which said transgene is packaged; wherein said minigene comprises AAV ITR sequences from a serotype heterologous to AAV5, and
    contacting the cells of the patient with a second rAAV, wherein the second rAAV comprising AAV 5' ITRs, a transgene comprising a nucleic acid sequence encoding a product which is under the control of regulatory sequences which direct expression of the product in a host cell, and AAV 3' ITRs, packaged in an AAV capsid which is from a serotype different from that of the rAAV5 capsid.

2. The method according to claim 1, wherein the minigene of the rAAV5 and/or the second rAAV comprises AAV2 sequences.

3. The method according to claim 1, wherein the recombinant adeno-associated virus serotype 5 vector comprises a 175 bp 5═ AAV5 inverted terminal repeat sequences and/or a 182 bp 3' AAV inverted terminal repeat sequences.

4. The method according to claim 1, rAAV5 sequences comprise a woodchuck hepatitis virus post-transcriptional element and a bovine growth hormone polyA signal downstream of the transgene.

5. The method according to claim 1, wherein the rAAV5 and/or the second rAAV is delivered to muscle.

6. The method according to claim 2, wherein the rAAV5 and/or the second rAAV is delivered to intestine.

* * * * *